(12) United States Patent
Fine et al.

(10) Patent No.: US 10,780,241 B2
(45) Date of Patent: Sep. 22, 2020

(54) DEVICES AND METHODS FOR MINIMIZING AND TREATING HIGH-ALTITUDE SICKNESS

(75) Inventors: David Fine, Cocoa Beach, FL (US);
Gregory Vasquez, Cocoa, FL (US);
Bryan Johnson, Orlando, FL (US)

(73) Assignee: VERO Biotech LLC, Atlanta, GA (US)

( * ) Notice: Subject to any disclaimer, the term of this patent is extended or adjusted under 35 U.S.C. 154(b) by 0 days.

(21) Appl. No.: 12/541,144

(22) Filed: Aug. 13, 2009

(65) Prior Publication Data
US 2010/0043788 A1    Feb. 25, 2010

Related U.S. Application Data

(60) Provisional application No. 61/090,617, filed on Aug. 21, 2008.

(51) Int. Cl.
| | | |
|---|---|---|
| *A61M 16/10* | (2006.01) | |
| *A61K 33/00* | (2006.01) | |
| *A61K 31/198* | (2006.01) | |
| *A61M 16/00* | (2006.01) | |
| *A61M 16/06* | (2006.01) | |

(52) U.S. Cl.
CPC .......... *A61M 16/10* (2013.01); *A61K 31/198* (2013.01); *A61K 33/00* (2013.01); *A61M 16/021* (2017.08); *A61M 16/0666* (2013.01); *A61M 16/107* (2014.02); *A61M 16/1075* (2013.01); *A61M 2202/0208* (2013.01); *A61M 2202/0275* (2013.01); *A61M 2202/03* (2013.01); *A61M 2205/3613* (2013.01)

(58) Field of Classification Search
CPC ...... A61M 16/00; A61M 16/12; A61M 16/10; A61M 16/104; A61M 16/14; A61M 16/16; A61M 2202/0275; A61M 2202/0283; A61K 33/00; A61K 33/198
USPC ............ 128/202.26, 203.12, 203.22, 204.14, 128/204.18, 205.25; 96/10; 239/6, 34; 141/31

See application file for complete search history.

(56) References Cited

U.S. PATENT DOCUMENTS

| | | | | | |
|---|---|---|---|---|---|
| 4,003,240 A | * | 1/1977 | Durbin | ..................... | G01N 7/00 122/4 R |
| 4,106,505 A | * | 8/1978 | Salter et al. | ............. | 128/207.18 |

(Continued)

FOREIGN PATENT DOCUMENTS

| | | |
|---|---|---|
| JP | 2004-275706 A | 10/2004 |
| WO | WO 92/10228 | 6/1992 |

(Continued)

OTHER PUBLICATIONS

"Kintek Trace Source Permeation Tubes," http://www.kin-tek.com/pdf/2_TraceSource.pdf, accessed Dec. 18, 2013.*

(Continued)

*Primary Examiner* — Colin W Stuart
*Assistant Examiner* — Douglas Y Sul

(57) ABSTRACT

A device and method for treating high-altitude sickness can include a handheld device, and can deliver a therapeutic amount of nitric oxide to an individual's lungs in order to minimize or treat high-altitude sickness. The device is self-contained and portable, which allows an individual to carry and use the device in high-altitude or other low-oxygen environments.

25 Claims, 5 Drawing Sheets

(56) References Cited

U.S. PATENT DOCUMENTS

| | | | |
|---|---|---|---|
| 4,998,431 A * | 3/1991 | Jappinen | G01N 33/0006 239/34 |
| 5,156,334 A * | 10/1992 | Kimbell et al. | 239/6 |
| 5,396,882 A | 3/1995 | Zapol et al. | |
| 5,485,827 A | 1/1996 | Zapol et al. | |
| 5,692,495 A * | 12/1997 | Sheu | 128/203.12 |
| 5,765,548 A * | 6/1998 | Perry | 128/200.24 |
| 5,777,203 A * | 7/1998 | Stymne | G01M 3/207 210/640 |
| 5,873,359 A | 2/1999 | Zapol et al. | |
| 5,972,369 A * | 10/1999 | Roorda | A61K 9/0004 424/424 |
| 6,269,811 B1 * | 8/2001 | Duff et al. | 128/204.21 |
| 6,758,214 B2 | 7/2004 | Fine et al. | |
| 7,025,869 B2 | 4/2006 | Fine et al. | |
| 7,399,449 B1 * | 7/2008 | Oborny | G01N 33/0006 422/504 |
| 2003/0230303 A1 | 12/2003 | Nichols et al. | |
| 2005/0005936 A1 * | 1/2005 | Wondka | 128/204.18 |
| 2006/0048779 A1 | 3/2006 | Rounbehler et al. | |
| 2006/0096596 A1 * | 5/2006 | Occhialini et al. | 128/204.18 |
| 2006/0180147 A1 * | 8/2006 | Rounbehler et al. | 128/203.12 |
| 2006/0207594 A1 | 9/2006 | Stenzler et al. | |
| 2007/0056584 A1 * | 3/2007 | Jagger et al. | 128/201.21 |
| 2008/0135044 A1 * | 6/2008 | Freitag et al. | 128/200.26 |

FOREIGN PATENT DOCUMENTS

| | | |
|---|---|---|
| WO | WO 93/17741 | 9/1993 |
| WO | 95/07610 | 3/1995 |
| WO | WO 03/59413 | 7/2003 |
| WO | WO 2006/023616 | 3/2006 |

OTHER PUBLICATIONS

"Matheson Gas Materials Compatibility Guide," http://www.mathesongas.com/pdfs/products/Materials-Compatibility-Guide.pdf, accessed Dec. 18, 2013.*

European supplementary search report for European Application No. 09808646.5 dated Jul. 19, 2012.

Anand et al., "Effects of Inhaled Nitric Oxide and Oxygen in High-Altitude Pulmonary Edema," Circulation, vol. 98, No. 22, Dec. 1, 1998, pp. 2441-2445.

Examination Report No. 1 for Australian Application No. 2009282985, dated May 26, 2014, 3 pages.

Office Action for European Application No. 09808646.5, dated Mar. 19, 2013, 4 pages.

International Search Report and Written Opinion for International Application No. PCT/US2009/053945, dated Sep. 22, 2009, 7 pages.

* cited by examiner

DEVICES AND METHODS FOR MINIMIZING AND TREATING HIGH-ALTITUDE SICKNESS

CLAIM OF PRIORITY

This application claims the benefit of prior U.S. Provisional Application No. 61/090,617, filed on Aug. 21, 2008, which is incorporated by reference in its entirety.

TECHNICAL FIELD

This description relates to devices and methods for minimizing and treating high-altitude sickness.

BACKGROUND

Exposure to low oxygen environments, typically found in high altitudes, may cause an individual to develop high-altitude sickness. High-altitude sickness can be relatively mild to life-threatening. A relatively mild form of high altitude sickness is acute mountain sickness, which is characterized by symptoms such as, but not limited to, headaches, breathlessness, fatigue, nausea, vomiting, or sleeplessness. Life-threatening forms of high-altitude sickness include high-altitude pulmonary edema (HAPE) and high-altitude cerebral edema (HACE). HAPE is characterized by symptoms such as pulmonary hypertension, increased pulmonary capillary permeability, and hypoxemia. HACE is characterized by changes in behavior, lethargy, confusion, and loss of coordination.

Typically, a mild case of high-altitude sickness is treated with rest, fluids, analgesics, or dexamethasone. More severe cases of high-altitude sickness can be treated with oxygen, hyperbaric therapy, or descent to lower elevations. While oxygen and hyperbaric therapies and descent to lower elevations provide relief from high-altitude sickness, these treatments have shortcomings. For example, oxygen therapy requires heavy, gas bottles that are difficult to carry in higher elevations. Hyperbaric therapy is less than ideal because this treatment requires specialized equipment and is labor-intensive. Lastly, descent to lower elevations may be not possible due to environmental factors or the poor physical condition of the individual. Accordingly, there remains a need for treatments of high-altitude sickness.

SUMMARY

Briefly, and in general terms, various embodiments are directed to methods and devices for minimizing and treating high-altitude sickness. The high altitude can be an altitude greater than 8,000 feet above sea level, greater than 10,000 feet above sea level, greater than 12,000 feet above sea level, greater than 14,000 feet above sea level, greater than 16,000 feet above sea level, greater than 18,000 feet above sea level, and higher.

According to one method, a therapeutic amount of nitric oxide (NO) is delivered to an individual's lungs when the individual is at high altitude. The delivery can take place before, during or after the onset of symptoms of high-altitude sickness. NO is inhaled continuously or intermittently for a few minutes to one or more days. In another method, air, oxygen-enriched air, or substantially pure oxygen may also be delivered with NO to treat high-altitude sickness.

The various methods of minimizing and treating high-altitude sickness may be carried out by one or more delivery devices disclosed herein. In one embodiment, a lightweight, handheld device permits self-administration of NO gas. The device includes a reservoir containing nitrogen dioxide ($NO_2$), a conversion cartridge coupled to the reservoir, and a patient interface coupled to the conversion cartridge. In one embodiment, the reservoir contains liquid dinitrogen tetroxide ($N_2O_4$), which is in equilibrium with $NO_2$ and serves as a liquid source of $NO_2$. In another embodiment, the reservoir stores a therapeutic amount of NO gas in nitrogen, air, oxygen-enriched air, or substantially pure oxygen. The conversion cartridge converts $NO_2$ into NO as $NO_2$ passes through the conversion cartridge.

Optionally, the delivery device may include a pump to deliver NO to an individual. The delivery device may also include a heating element associated with the conversion cartridge (and optionally the reservoir) in order to keep the device at operating temperatures in cold weather environments. Alternatively, the liquid $N_2O_4$ reservoir and the conversion cartridge are worn close to the body, so as to remain at a constant temperature above about 5° C.

In another embodiment, the delivery device is a stand-alone gas bottle having a conversion cartridge and a patient interface. Optionally, the delivery device includes a recuperator provided in the gas plumbing line prior to the patient interface. The patient interface may be a respirator, ventilator, nasal cannula, or mouth piece. The patient interface also may include a gas bag or other temporary gas storage device. According to one embodiment, the delivery device includes a housing that operably couples the gas bottle to the conversion cartridge. In another embodiment, the housing includes a regulator gauge and valve for adjusting gas pressure from the gas bottle. Additionally, the housing includes an integral handle that enhances the portability of the delivery device.

In yet another embodiment, a conversion cartridge for converting nitrogen dioxide into nitric oxide is disclosed herein. The conversion cartridge includes a body having a first end and second end. The body contains a surface-activated material saturated with an aqueous solution of an antioxidant that converts $NO_2$ into NO. The first end of the body is sized to engage a source of $NO_2$, $N_2O_4$, or NO, and the second end of the body is engagable with a patient interface or direct patient contact.

Other features will become apparent from the following detailed description, taken in conjunction with the accompanying drawings, which illustrate by way of example, the features of the various embodiments.

DETAILED DESCRIPTION

Figure 1:
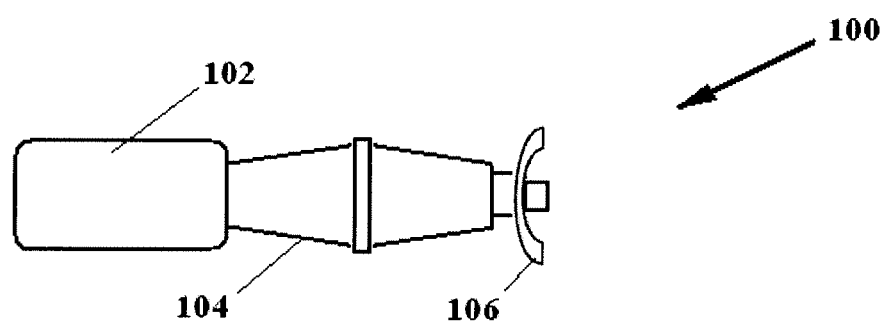
FIG. 1 is a side view of one embodiment of a NO delivery device.

Low oxygen environments such as those in high altitude locations reduce the partial arterial pressure in the lungs which can consequently lead to acute hypoxic pulmonary vasoconstriction (HPV) and hypoxemia (deficiency in the concentration of dissolved oxygen in arterial blood). HPV is a physiological phenomenon in which pulmonary arteries constrict in the presence of hypoxia (low oxygen levels) without high carbon dioxide levels, redirecting blood flow to alveoli with higher oxygen tension. HPV may have profound hemodynamic consequences, including a reduction in cardiac output, pulmonary edema and right ventricular failure, but it is reversible if adequate alveolar oxygenation can be re-established.

In the early phase of exposure to high altitude, signs of acute mountain sickness (AMS) may develop and have been shown to be worsened by aggravating hypoxemia, although the precise mechanisms of AMS is not clear. AMS is defined as a headache in an un-acclimated person who has recently arrived at an altitude above 3000 m plus and the presence of one or more of the following: a) gastrointestinal symptoms like anorexia, nausea or vomiting, b) insomnia, c) dizziness and d) exhaustion or fatigue. It is the most common type of high altitude sickness, typically developing symptoms within 6 to 10 hours. The importance of AMS lies in its early recognition as it may progress to High Altitude Cerebral Edema (HACE), clinically identified with lack of coordination of muscle movement, altered consciousness or both in a person suffering from AMS.

High Altitude Pulmonary edema (HAPE), a more dangerous outcome of hypoxemia, accounts for most deaths from high altitude sickness and 44% of untreated cases. Most cases appear on the second and third day of arrival at high elevation and are more frequent in young, fit climbers or trekkers. Symptoms consist of shortness of breath with exercise, progressing to shortness of breath at rest, a dry cough, weakness and poor exercise tolerance. As the disease worsens, pulmonary edema is obvious, followed by coma and death. As in other high-altitude sicknesses, the incidence of HAPE is related to the rate of ascent, the altitude reached, individual susceptibility. Even mild HAPE can have a pronounced effect upon exercise intensity, finding even the simplest task exhausting.

The management of high altitude sickness requires correction of hypoxemia and interventions to reduce pulmonary arterial or cerebral pressure. The most effective treatment is descent to lower altitude. Currently, there is no approved treatment for altitude induced hypoxemia when immediate descent is not possible.

Various embodiments are directed to methods and devices for minimizing and treating high-altitude sickness. Generally, nitric oxide (NO) is inhaled or otherwise delivered to the individual's lungs. NO is used to minimize symptoms and/or prevent high-altitude sickness. Providing a therapeutic dose of NO would supplement or minimize the need for traditional treatments including, but not limited to, oxygen therapy or rapid descent to lower elevations to treat symptoms of high-altitude sickness. Additionally, NO treatment allows the individual to sustain higher levels of physical activity in higher elevations. For example, a hiker would be able to continue ascending a mountain or a soldier can maintain stamina and performance during high-altitude combat operations. Alternatively, NO may be provided to pilots and passengers in the event of a loss in cabin pressure. Optionally, a combination of NO and pure oxygen, oxygen-enriched air (e.g., approximately 90 to 99.9 percent oxygen), or pure oxygen may be used to treat high-altitude sickness.

Home oxygen therapy is administered to many people who cannot get enough oxygen from the air. This treatment is effective, but the patient's mobility is limited since the treatment requires bulky and/or heavy equipment such as a home oxygen generator, a gas bottle containing pressurized oxygen, or a bottle that contains liquid oxygen, which is vaporized into the gaseous state just prior to inhalation. Accordingly, a light, portable device for delivering NO with air has the potential to improve a patient's quality of life. The device may be powered by a small, battery-driven pump or by patient inhalation (similar to smoking a cigar). Additionally, a treatment providing NO (e.g., converting $N_2O_4$ into NO) would be more cost effective than oxygen therapy.

Currently, approved devices and methods for delivering inhaled NO gas require complex and heavy equipment. NO gas is stored in heavy gas bottles with nitrogen and no traces of oxygen. The NO gas is mixed with air or oxygen with specialized injectors and complex ventilators, and the mixing process is monitored with equipment having sensitive microprocessors and electronics. All this equipment is required in order to ensure that NO is not oxidized into nitrogen dioxide ($NO_2$) during the mixing process since $NO_2$ is highly toxic. However, this equipment is not conducive to use in a non-medical facility setting (e.g., combat operations or remote wilderness) since the size, cost, complexity, and safety issues restrict the operation of this equipment to highly-trained professionals in a medical facility.

In contrast, the delivery devices disclosed herein are self-contained, portable systems that do not require heavy gas bottles, sophisticated electronics, or monitoring equipment. Additionally, the delivery devices are easy to use and do not require any specialized training. Moreover, the delivery devices allow an individual to self-administer a NO treatment. The delivery devices are also lightweight, compact, and portable. According to one embodiment, the NO delivery device is the size of a cigar or a conventional inhaler for one-time use or short-term treatments. Alternatively, the NO delivery device is a larger device, yet portable device that can deliver NO for longer periods of time.

As shown in FIG. 1, the NO delivery device 100 includes a reservoir 102. Generally, the reservoir 102 supplies NO lasting a few minutes to one or more days of continuous use, depending upon the method of storing the NO. In one embodiment, the reservoir 102 stores a therapeutic amount of $NO_2$ that is converted into NO. The therapeutic amount of NO is diluted to the necessary concentration and stored with air, oxygen-enriched air, or substantially pure oxygen. In another embodiment for long-term use for many days, the NO is stored as liquid dinitrogen tetraoxide ($N_2O_4$) in a diffusion tube of a permeation tube that is vaporizable into $NO_2$, typically, which in turn, is converted into NO.

In various embodiments, the reservoir 102 is sized to hold a few milligrams to tens of grams of liquid $N_2O_4$. For short-term treatments, the reservoir 102 is sized to contain a few milligrams of $N_2O_4$. For example, the reservoir 102 may be sized to hold approximately 7 mg of $N_2O_4$ (1), which would provide 20 ppm of NO for ten minutes. For long-term applications, the reservoir 102 may be sized to contain 10 or more g of $N_2O_4$ for long-term use such as several weeks. For example, a reservoir containing approximately 0.3 g of $N_2O_4$ may provide 20 ppm of NO at 20 L/min. for 24 hours, and a reservoir containing 10 g of $N_2O_4$ would provide a continuous supply of NO for approximately 30 days. In other examples, the reservoir 102 is sized to hold less then 1 ml, 2 ml, 3 ml, 4 ml, 5 ml, 10 ml of liquid $N_2O_4$.

FIG. 1 illustrates the conversion cartridge 104 directly coupled to (and detachable from) a patient interface 106. In one embodiment, the patient interface 106 is an integral piece of the conversion cartridge 104. For example, one end of the conversion cartridge 104 may be molded and shaped as a mouth piece or nasal cannula. In another embodiment, patient interface (not shown) is simply an opening at the second end of the conversion cartridge 104. In yet another embodiment, the second end of the conversion cartridge 104 is shaped and sized to receive gas tube plumbing (or other conduits known or developed in the art) that includes a mouth piece, nasal cannula, face mask, or fully-sealed face mask.

Figure 2:
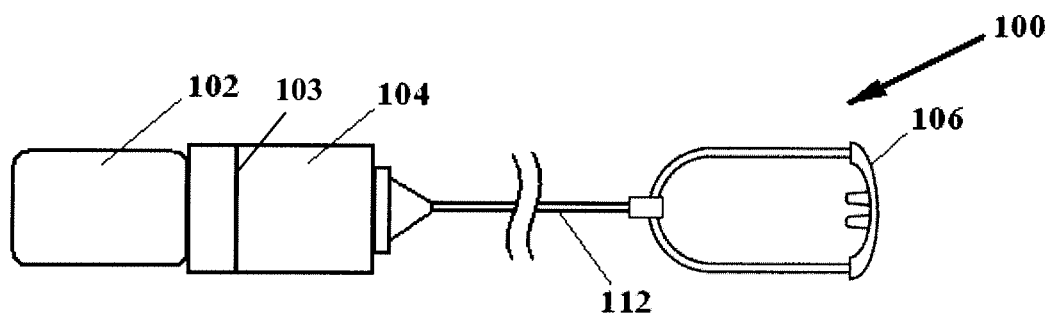
FIG. 2 is a side view of another embodiment of a NO delivery device.

As shown in FIG. 1, the reservoir 102 is connected to one end of the conversion cartridge 104 in linear orientation. In other embodiments, the reservoir 102 is approximately perpendicular to cartridge 104 or the reservoir is angled with respect to the cartridge. Additionally, as shown in FIG. 1, the various components 102, 104, 106 are directly coupled to one another. It is also contemplated that one or more of the components of the device 100 may not be directly connected together. For example, referring to FIG. 2, varying lengths of gas line plumbing 112 (or other conduits) may be used to connect the various components 102, 104, 106 of the device 100. In FIG. 2, the patient interface 106 is not directly connected to the conversion cartridge 104, but the patient interface is connected to conversion cartridge via gas line plumbing 112. This approach would be used, for example, in temperatures below freezing so that components 102 and 104 can be stored under clothing to maintain the temperature above freezing. Ideally, the component 102 needs to be held at approximately a constant temperature which can be maintained by being in contact with the body or in close proximity to the body. If component 102 contains liquid $N_2O_4$, then in order to maintain a constant concentration of NO, it should be maintained at approximately a constant temperature. This is best carried out by keeping component 102 in close proximity to the body.

Figure 3A:
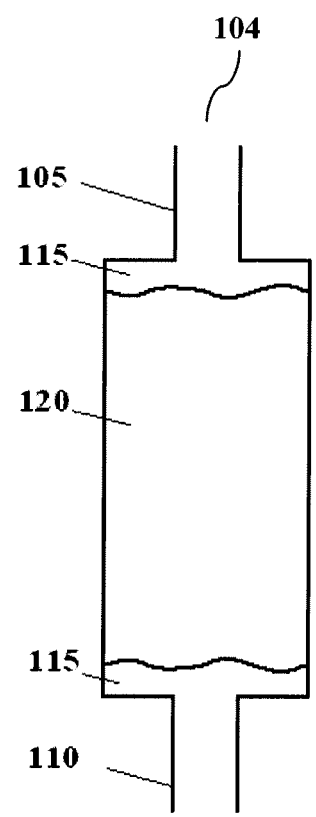
FIG. 3A is a block diagram of a cartridge that converts $NO_2$ to NO.
Figure 3B:
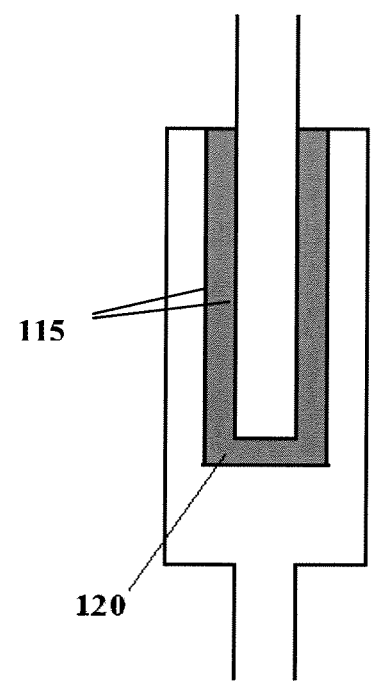
FIG. 3B is a block diagram of another embodiment of a cartridge that converts $NO_2$ to NO.

FIG. 3A illustrates one embodiment of a conversion cartridge 104 that generates NO from $NO_2$. The conversion cartridge 104 also may be referred to as a NO generation cartridge, a GENO cartridge, or a GENO cylinder. The conversion cartridge 104 includes an inlet 105 and an outlet 110. In one embodiment a particle filter 115 is located at both the inlet 105 and the outlet 110, and the remainder of the cartridge 104 is filled with a surface-active material 120 that is soaked with a saturated solution of antioxidant in water to coat the surface-active material. In another embodiment, illustrated in FIG. 3B, the particulate filter 115 may be in the form of two concentric annular filters with the surface-active material 120 placed between the two annular filters. In this embodiment the gas flows from the inside of the annulus to the outside, or vice versa. In another embodiment, the surface-active material 120 and the filter material 115 are cast into one solid matrix as a sintered tube. In the examples of FIG. 3A and FIG. 3B FIG. 3, the antioxidant is ascorbic acid.

In a general process for converting $NO_2$ to NO, an air flow having $NO_2$ is received through the inlet 105 and the air flow is fluidly communicated to the outlet 110 through the surface-active material 120 coated with the aqueous antioxidant. As long as the surface-active material remains moist and the antioxidant has not been used up in the conversion, the general process is effective at converting $NO_2$ to NO at ambient temperatures.

The inlet 105 may receive the air flow having $NO_2$, for example, from a pressurized bottle of $NO_2$, which also may be referred to as a tank of $NO_2$. The inlet 105 also may receive an air flow with $NO_2$ in nitrogen ($N_2$), air, or oxygen ($O_2$). The inlet 105 may also receive the air flow having $NO_2$ from an air pump that fluidly communicates an air flow over a permeation tube 235 containing liquid $N_2O_4$, such as in the device 200 of FIG. 4. The conversion occurs over a wide concentration range. Experiments have been carried out at concentrations in air of from about 0.2 ppm $NO_2$ to about 100 ppm $NO_2$, and even to over 1000 ppm $NO_2$. In one example, a cartridge that was approximately 5 inches long and had a diameter of 0.8-inches was packed with silica gel that had first been soaked in a saturated aqueous solution of ascorbic acid. Other sizes of the cartridge are also possible. The moist silica gel was prepared using ascorbic acid (i.e., vitamin C) designated as A.C.S reagent grade 99.1% pure from Aldrich Chemical Company and silica gel from Fischer Scientific International, Inc., designated as S8 32-1, 40 of Grade of 35 to 70 sized mesh. Other similar sizes of silica gel also are effective, provided that the particle size and the pore size within the particles are similar.

The silica gel was moistened with a saturated solution of ascorbic acid that had been prepared by mixing up to 35% by weight ascorbic acid in water, stirring, and straining the water/ascorbic acid mixture through the silica gel, followed by draining. It has been found that the conversion of $NO_2$ to NO proceeds well when the silica gel coated with ascorbic acid is moist. The conversion of $NO_2$ to NO does not proceed well in an aqueous solution of ascorbic acid alone.

The cartridge filled with the wet silica gel/ascorbic acid was able to convert 1000 ppm of $NO_2$ in air to NO at a flow rate of 150 ml per minute, quantitatively, non-stop for over 12 days. A wide variety of flow rates and $NO_2$ concentrations have been successfully tested, ranging from only a few ml per minute to flow rates of up to 5,000 ml per minute. Using an annular cartridge, flow rates of up to 60,000 ml per minute have been used. The reaction also proceeds using other common antioxidants, such as variants of vitamin E (e.g., alpha tocopherol and gamma tocopherol).

The antioxidant/surface-active material GENO cartridge may be used for treating high-altitude sickness. In one such example, the GENO cartridge may be used as a $NO_2$ scrubber for NO inhalation therapy that delivers NO from a pressurized bottle source. The GENO cartridge not only scrubs the $NO_2$ but converts the $NO_2$ back into NO gas, which is then inhaled by the patient. This cartridge is also referred to as a recuperator. This GENO cartridge may be used to help ensure that no harmful levels of $NO_2$ are inadvertently inhaled by the patient. Additionally, the GENO cartridge ensures that the patient is receiving the entire NO dose as NO gas and not as the toxic form, $NO_2$.

Figure 4:
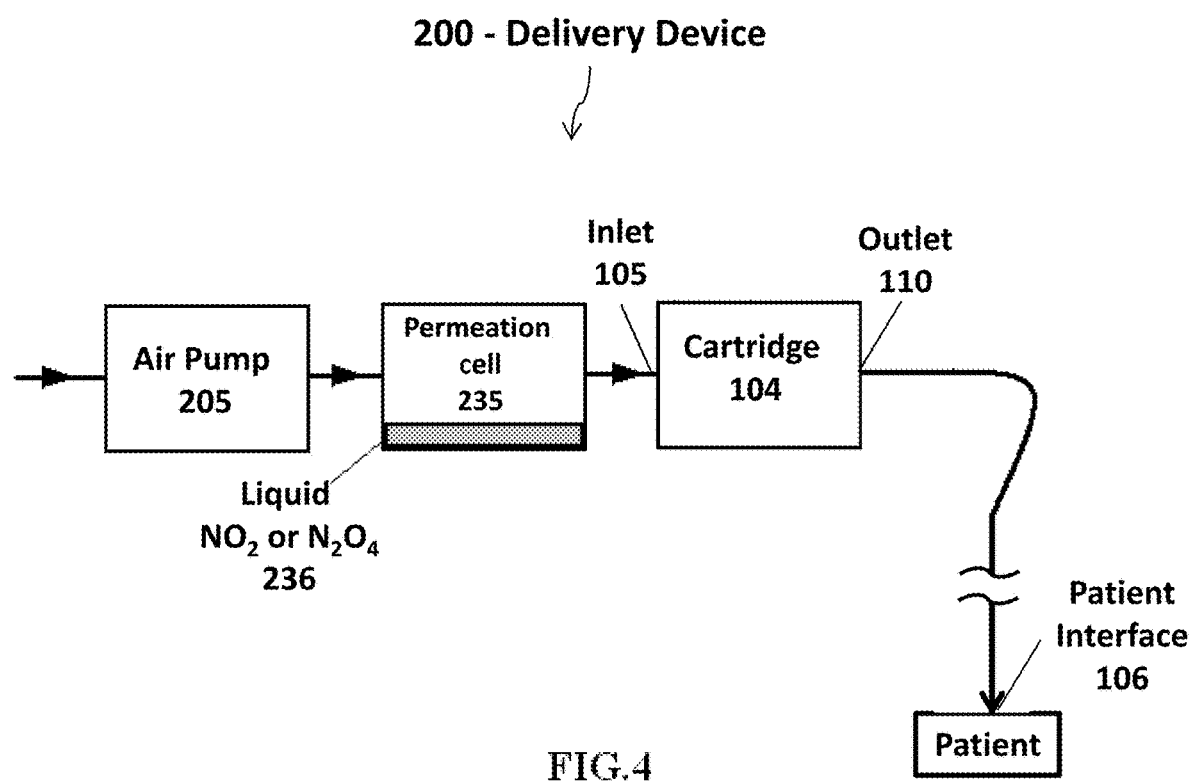
FIG. 4 is a block diagram of another embodiment a NO delivery device.

FIG. 4 is a block diagram of an embodiment of a delivery device 200 having a gas permeation cell 235. In general, a flow of air is passed through a gas permeation cell 235 having liquid $NO_2$ and its dimer $N_2O_4$ (collectively, 236). The permeation cell 235 also may be referred to as a permeation generator, a permeation device or a permeation tube holder. A diffusion tube may also be used instead of a permeation tube. The air flow exiting the gas permeation cell 235 includes gaseous $NO_2$, which is converted to NO gas by a NO generation cartridge 104. The NO gas mixture may be delivered to a patient for inhalation therapy, for example, using a mask or a cannula. The concentration of NO in the NO gas mixture delivered to the patient may be controlled by controlling the temperature of the gas permeation cell 235 or the air flow rate of the pump.

According to one embodiment, the permeation tube 237 is designed to release $NO_2$ at a steady rate such that the gas stream leaving the permeation tube contains about 20 ppm of $NO_2$ at a flow rate of approximately 20,000 ml per minute, when the temperature of the permeation tube is approximately 20° C. As those skilled in the art will appreciate, maintaining the temperature of the permeation cell 235 or the diffusion tube helps to control the concentration of NO delivered to the patient.

Optionally, the delivery devices 100, 200 may include a pump 103 to move $NO_2$ gas from the reservoir 102 or the permeation cell 235 through the conversion cartridge 104. The pump 103 may be battery operated, solar powered, or crank powered. Alternately, $NO_2$ gas is drawn through the conversion cartridge 104 (and the diffusion or permeation cell 235) by the individual applying a suctioning force at the second end of the conversion cartridge. In another embodiment, the reservoir 102 is a high pressure vessel containing compressed gas. When a valve (not shown) is actuated, $NO_2$ gas is expelled from the reservoir 102 through the conversion cartridge 104, thereby converting the $NO_2$ gas into NO prior to inhalation. In those embodiments where the reservoir 102 stores NO, the conversion cartridge 104 ensures that any inhaled NO is devoid of $NO_2$.

In another embodiment, the delivery devices 100, 200 may also include a heating element for use in cold weather environs (e.g., less than approximately 5° C. or those temperatures in which the antioxidant-water combination would freeze and or the $N_2O_4$ would freeze). The heating element is associated with the conversion cartridge 104 or the gas permeation cell 235. The heating element may be electrically, chemically, or solar powered. Alternatively, the conversion cartridge 104 or the diffusion tube are strapped or otherwise held close to an individual's body in order to utilize the individual's body heat to keep the conversion cartridge and the diffusion tube at operating temperatures (i.e., those temperatures that where $NO_2$ has sufficient vapour pressure and ascorbic acid-water remains a liquid), and to ensure that the dose of NO is adequate.

Figure 5:
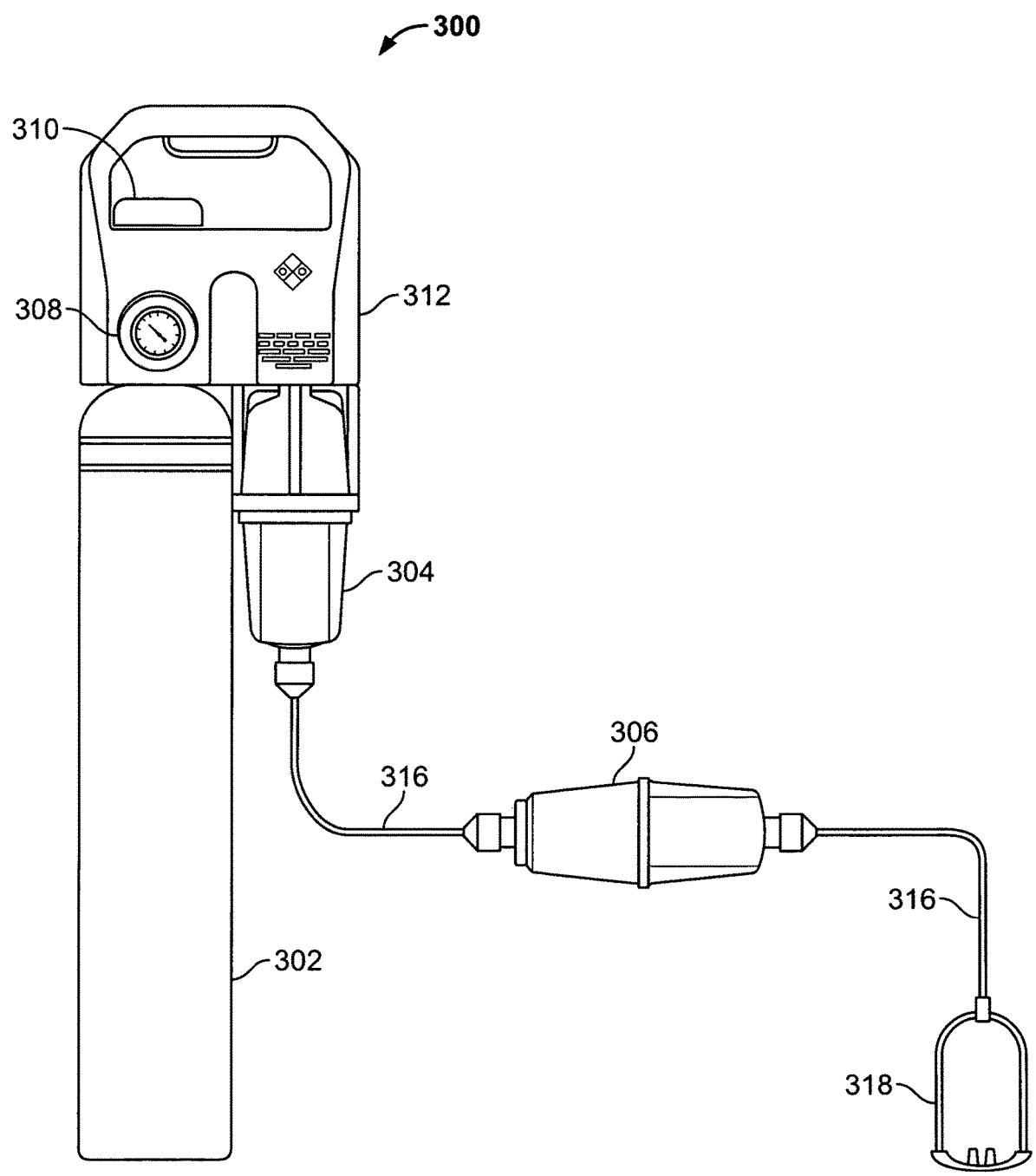
FIG. 5 is a side view of yet another embodiment of a NO delivery device.

FIG. 5 illustrates another embodiment of a delivery device 300. The delivery device 300 includes a stand-alone gas bottle 302 having a conversion cartridge 304 and a recuperator 306. The stand-alone gas bottle 302 may contain $NO_2$ in nitrogen, air, or oxygen-enriched air. $NO_2$ gas may be diluted to a therapeutic dosage in the stand-alone gas bottle 302 or liquid $NO_2$ and its dimer $N_2O_4$ may be contained within the bottle. The outlet of the bottle is coupled to a regulator having a gauge 308 and a valve 310. As shown in FIG. 5, the regulator 308 is a component within a body 312 that includes a handle 314 and a port (not shown) for engaging a conversion cartridge 304. As shown in this device, a recuperator 306 is placed within the gas plumbing line 316 just prior to the patient interface 318. The recuperator 306 converts any $NO_2$ gas that may have been formed in the patient interface 318 back into NO gas. As shown in FIG. 5, the patient interface 318 is a nasal cannula, but it is contemplated that the patient interface may be a mouth piece, a cannula, ventilator, a gas bag, or face mask.

Figure 6:
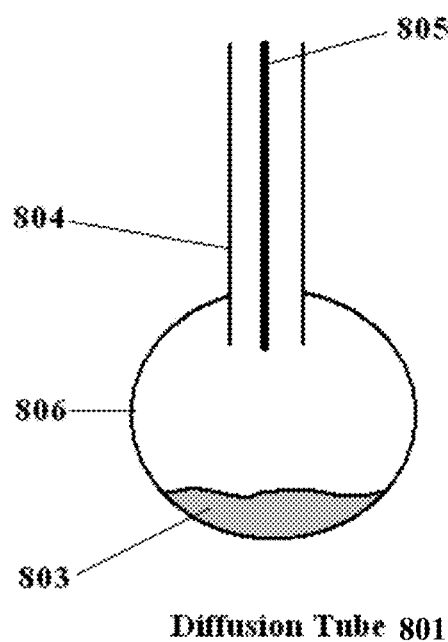
FIG. 6 is a block diagram of one embodiment of a diffusion tube.

FIG. 6 is a diagram of one type of diffusion tube 801 that can be used. The reservoir component 806 and the narrow bore tube, component 804 are manufactured from a material that is not attacked chemically by $N_2O_4$ and $NO_2$. Stainless steel is a suitable material. The interior of reservoir 806 of the diffusion tube 801 has a spherical shape and the tube 804 extends into the reservoir 806 for the purpose of preventing the liquid $N_2O_4$, component 803, from being transferred into the tube. This arrangement allows the device to function at any orientation and to withstand vibration. Component 805 is the narrow bore capillary tube that connects the reservoir 806 with the environment. The diameter and length of the tube define the diffusion rate from the diffusion tube if the temperature remains constant.

The various embodiments described above are provided by way of illustration only and should not be construed to limit the claimed invention. Those skilled in the art will readily recognize various modifications and changes that may be made to the claimed invention without following the example embodiments and applications illustrated and described herein, and without departing from the true spirit and scope of the claimed invention, which is set forth in the following claims.

What is claimed:

1. An apparatus comprising:
    a diffusion tube including:
        a reservoir configured to contain liquid dinitrogen tetroxide ($N_2O_4$) and having a gas space configured to be filled with gaseous nitrogen dioxide ($NO_2$) in equilibrium with the $N_2O_4$ when the reservoir contains the liquid $N_2O_4$; and
        a conduit constructed of a material impermeable to the gaseous $NO_2$ extending into the gas space of the reservoir, the conduit defining a narrow bore capillary tube having a first end in direct contact with the gas space directly over a surface of the liquid $NO_2$, a diffusion rate of the gaseous $NO_2$ from the diffusion tube being constant and defined by a diameter and a length of the narrow bore capillary tube if temperature remains constant;
    coupled to a second end of the narrow bore capillary tube, the conversion cartridge configured to convert the gaseous $NO_2$ into gaseous nitric oxide (NO); and
    a patient interface coupled to the conversion cartridge and configured to deliver the gaseous NO to a patient.

2. The apparatus of claim 1, further comprising a pump in communication with the reservoir.

3. The apparatus of claim 1, wherein the patient interface is a mouthpiece, nasal cannula, face mask, or fully-sealed face mask.

4. The apparatus of claim 1, wherein the reservoir is in fluid communication with a source of at least one of nitrogen, air, oxygen-enriched air, or substantially pure oxygen, such that the gas space of the reservoir is configured to contain a mixture of the gaseous $NO_2$ and the at least one of nitrogen, air, oxygen-enriched air, or substantially pure oxygen.

5. The apparatus of claim 1, wherein the conversion cartridge includes a surface-activated material wetted with an aqueous solution of an antioxidant.

6. The apparatus of claim 5, wherein the surface-activated material is a silica gel.

7. The apparatus of claim 5, wherein the antioxidant is at least one of ascorbic acid, alpha tocopherol, or aamma tocopherol.

8. The apparatus of claim 1, wherein the patient interface is a delivery tube adapted to contact the patient's mouth or nose.

9. The apparatus of claim 1, wherein the reservoir contains compressed nitrogen dioxide and a diluent gas.

10. The apparatus of claim 1, wherein the conversion cartridge is configured to convert the gaseous $NO_2$ into the gaseous NO at a flow rate of less than 60 L/min.

11. The apparatus of claim 10, further comprising a pump in communication with the reservoir.

12. The apparatus of claim 11, wherein the pump is a battery-driven pump.

13. The apparatus of claim 10, wherein the patient interface is a mouthpiece, nasal cannula, face mask, or fully-sealed face mask.

14. The apparatus of claim 10, wherein the reservoir is in fluid communication with a source of at least one of nitrogen, air, oxygen-enriched air, or substantially pure oxygen, such that the gas space of the reservoir is configured to contain a mixture of the gaseous $NO_2$ and the at least one of nitrogen, air, oxygen-enriched air, or substantially pure oxygen.

15. The apparatus of claim 10, wherein the conversion cartridge includes a surface-activated material wetted with an aqueous solution of an antioxidant.

16. The apparatus of claim 15, wherein the surface-activated material is a silica gel.

17. The apparatus of claim 15, wherein the antioxidant is at least one of ascorbic acid, alpha tocopherol, or gamma tocopherol.

18. Apparatus of claim 10, wherein the reservoir contains compressed nitrogen dioxide and a diluent gas.

19. The apparatus of claim 1, wherein the patient interface is a nasal cannula.

20. The apparatus of claim 1, wherein the conversion cartridge includes:

at least two concentric annular particle filters; and a surface-active material wetted with a solution of antioxidant in water.

21. The apparatus of claim 1, wherein the conversion cartridge includes a particle filter and a surface-active material wetted with a solution of antioxidant in water cast as a solid matrix.

22. The apparatus of claim 1, further comprising a heating element associated with the reservoir.

23. The apparatus of claim 1, wherein the conversion cartridge is configured to convert the gaseous $NO_2$ into the gaseous NO at ambient temperatures.

24. The apparatus of claim 1, wherein the conduit that defines the narrow bore capillary tube is constructed of stainless steel.

25. The apparatus of claim 1, wherein the reservoir has a spherical shape such that the diffusion tube is configured to function at any orientation and to withstand vibration.

* * * * *

UNITED STATES PATENT AND TRADEMARK OFFICE
CERTIFICATE OF CORRECTION

PATENT NO. : 10,780,241 B2
APPLICATION NO. : 12/541144
DATED : September 22, 2020
INVENTOR(S) : David H. Fine et al.

It is certified that error appears in the above-identified patent and that said Letters Patent is hereby corrected as shown below:

In the Claims

Column 8, Line 28 (Claim 1, Line 17): "coupled" should be --a conversion cartridge coupled--;

Column 8, Line 51 (Claim 7, Line 2): "aamma" should be --gamma--;

Column 8, Line 60 (Claim 10, Line 3): after "60/L/min", add --prior to reaching the patient interface--.

Signed and Sealed this
Seventeenth Day of May, 2022

Katherine Kelly Vidal
*Director of the United States Patent and Trademark Office*